United States Patent
Bae et al.

(10) Patent No.: US 10,624,646 B2
(45) Date of Patent: Apr. 21, 2020

(54) CIRCULAR STAPLER

(71) Applicant: BNR CO., LTD., Incheon (KR)

(72) Inventors: Gyeongcheol Bae, Seoul (KR); Sungki Min, Seoul (KR); Gichang Kim, Seoul (KR); Bonggwan Jeon, Gyeonggi-do (KR); Hoe Chan Kim, Incheon (KR); Sujin Bae, Seoul (KR); Junghwa Hong, Seoul (KR)

(73) Assignee: BNR CO., LTD., Incheon (KR)

( * ) Notice: Subject to any disclaimer, the term of this patent is extended or adjusted under 35 U.S.C. 154(b) by 404 days.

(21) Appl. No.: 15/425,001

(22) Filed: Feb. 6, 2017

(65) Prior Publication Data

US 2018/0116667 A1 May 3, 2018

(30) Foreign Application Priority Data

Oct. 31, 2016 (KR) .......................... 10-2016-0143031

(51) Int. Cl.
  *A61B 17/115* (2006.01)
  *A61B 17/072* (2006.01)
  *A61B 90/00* (2016.01)
  *A61B 17/00* (2006.01)

(52) U.S. Cl.
  CPC .... *A61B 17/1155* (2013.01); *A61B 17/07207* (2013.01); *A61B 2017/00115* (2013.01); *A61B 2017/07221* (2013.01); *A61B 2017/07257* (2013.01); *A61B 2017/07271* (2013.01); *A61B 2090/065* (2016.02); *A61B 2562/04* (2013.01); *A61B 2562/16* (2013.01)

(58) Field of Classification Search
  CPC ...... A61B 17/1155; A61B 2017/07214; A61B 17/115
  See application file for complete search history.

(56) References Cited

U.S. PATENT DOCUMENTS

| 4,564,730 | A | * | 1/1986 | Tomizu | H01H 1/58 |
| | | | | | 200/16 B |
| 4,703,140 | A | * | 10/1987 | Poling | H01H 35/34 |
| | | | | | 200/83 J |
| 4,721,507 | A | * | 1/1988 | Chin | A61B 17/3207 |
| | | | | | 600/587 |
| 5,965,880 | A | * | 10/1999 | Wolf | G01L 5/228 |
| | | | | | 250/227.14 |

(Continued)

FOREIGN PATENT DOCUMENTS

KR    10-2011-0086948    8/2011

*Primary Examiner* — Nathaniel C Chukwurah
*Assistant Examiner* — Lucas E. A. Palmer
(74) *Attorney, Agent, or Firm* — Duane Morris LLP; J. Rodman Steele, Jr.; Gregory M. Lefkowitz

(57) ABSTRACT

Disclosed is a circular stapler. The circular stapler includes a head cover (100) formed in a tubular shape so that a space is defined therein, a cartridge (200) provided in one end of the head cover (100) to accommodate a staple therein, a staple drive (300) provided inside the head cover (100) to extrude the staple from the cartridge (200) while moving toward the cartridge (200), a sensor drive (400) provided inside the head cover (100) and configured to come into contact with the cartridge (200), and a pressure sensor (500) provided inside the head cover (200) to measure pressure applied to the cartridge (200) by receiving the pressure from the sensor drive (400).

13 Claims, 7 Drawing Sheets

(56) References Cited

U.S. PATENT DOCUMENTS

| | | | | |
|---|---|---|---|---|
| 6,518,528 B2* | 2/2003 | Nickerson | H01H 3/16 | 200/16 A |
| 7,691,056 B2* | 4/2010 | Hirata | A61B 1/00096 | 600/117 |
| 7,717,312 B2* | 5/2010 | Beetel | A61B 17/068 | 227/175.1 |
| 8,694,069 B1* | 4/2014 | Kosa | A61B 5/1455 | 264/1.24 |
| 9,420,967 B2* | 8/2016 | Zand | A61B 5/14552 | |
| 10,265,066 B2* | 4/2019 | Measamer | A61B 17/068 | |
| 2004/0030335 A1* | 2/2004 | Zenati | A61B 17/12013 | 606/51 |
| 2004/0143162 A1* | 7/2004 | Krattiger | A61B 1/00096 | 600/175 |
| 2004/0153124 A1* | 8/2004 | Whitman | A61B 17/07207 | 606/219 |
| 2007/0175964 A1* | 8/2007 | Shelton, IV | A61B 17/072 | 227/180.1 |
| 2007/0267281 A1* | 11/2007 | Smith | A61B 17/00 | 200/61.53 |
| 2007/0270784 A1* | 11/2007 | Smith | A61B 17/1114 | 606/1 |
| 2008/0319268 A1* | 12/2008 | Michaeli | A61B 17/0218 | 600/202 |
| 2009/0054908 A1* | 2/2009 | Zand | A61B 5/0071 | 606/130 |
| 2009/0234248 A1* | 9/2009 | Zand | A61B 5/0031 | 600/587 |
| 2011/0295270 A1* | 12/2011 | Giordano | A61B 17/00234 | 606/130 |
| 2012/0138658 A1* | 6/2012 | Ullrich | A61B 17/072 | 227/175.1 |
| 2013/0014595 A1* | 1/2013 | Huizinga | B60T 17/22 | 73/862.045 |
| 2014/0114327 A1* | 4/2014 | Boudreaux | A61B 18/1445 | 606/130 |
| 2014/0309665 A1* | 10/2014 | Parihar | A61B 17/1155 | 606/139 |
| 2015/0316431 A1* | 11/2015 | Collins | A61B 90/98 | 606/219 |
| 2016/0066911 A1* | 3/2016 | Baber | A61B 5/6847 | 307/52 |
| 2016/0066913 A1* | 3/2016 | Swayze | A61B 17/072 | 227/176.1 |
| 2016/0066916 A1* | 3/2016 | Overmyer | A61B 17/105 | 227/176.1 |
| 2016/0265938 A1* | 9/2016 | Hryb | A61B 5/6847 | |
| 2016/0296234 A1* | 10/2016 | Richard | A61B 17/1155 | |
| 2016/0310134 A1* | 10/2016 | Contini | A61B 17/07207 | |
| 2017/0164947 A1* | 6/2017 | Williams | A61B 17/1155 | |
| 2017/0224347 A1* | 8/2017 | Collins | A61B 17/1155 | |
| 2017/0238991 A1* | 8/2017 | Worrell | A61B 18/1445 | |
| 2017/0296184 A1* | 10/2017 | Harris | A61B 17/07207 | |
| 2018/0042610 A1* | 2/2018 | Sgroi, Jr. | A61B 17/0684 | |
| 2018/0067004 A1* | 3/2018 | Sgroi, Jr. | G01L 1/26 | |
| 2018/0098768 A1* | 4/2018 | Zhang | A61B 17/072 | |
| 2018/0249999 A1* | 9/2018 | Parihar | A61B 17/1155 | |
| 2018/0338383 A1* | 11/2018 | Sgroi, Jr. | H05K 5/0247 | |
| 2018/0353186 A1* | 12/2018 | Mozdzierz | A61B 17/1155 | |

* cited by examiner

CIRCULAR STAPLER

CROSS-REFERENCE TO RELATED APPLICATIONS

This application claims, under 35 U.S.C. § 119, the priority of Korean Patent Application No. 10-2016-0143031 filed on Oct. 31, 2016 in the Korean Intellectual Property Office, the disclosure of which is incorporated herein by reference in its entirety.

BACKGROUND OF THE INVENTION

Field of the Invention

The present invention relates to a circular stapler.

Description of the Related Art

Research conducted by the International Agency for Research on Cancer (IARC) related to the incidence of cancer in 184 countries based on the population index of the European Union (EU) shows that the incidence of colorectal cancer has greatly increased in recent years, and on the basis of which the number of patients expected to contract cancer will increase to 22.2 million people, which is 0.3% of the world's population by 2030.

In Korea, cancer is also ranked as the No. 1 cause of death of both males and females. Among various kinds of cancer, the incidence of rectal cancer and colorectal cancer is increasing year over year, and the development of a stapler that has high safety and perfection for surgical treatment performed in response to rectal cancer or colorectal cancer is urgently needed. In particular, the need for such a stapler will rapidly expand as the baby boomer population is now becoming elderly.

As disclosed in the following patent document describing the related art, a surgical operation using a stapler known in the related art depends on the experience and intuition of an operator. Therefore, leakage due to insufficient stapler contact pressure, stenosis/necrosis due to excessive stapler contact pressure, and the like may occur. In order to prevent such clinical problems (e.g. leakage, stenosis and necrosis), the contact pressure of a stapler needs to be appropriately adjusted when treating enteroanastomosis, but research related thereto has not been thoroughly conducted.

PRIOR ART DOCUMENT

Patent Document (Patent Document 1) KR10-2011-0086948 A

SUMMARY OF THE INVENTION

Therefore, the present invention has been made in view of the above problems, and it is an object of the present invention to provide a circular stapler, which may appropriately adjust the contact pressure thereof when used to treat enteroanastomosis by measuring the stapler contact pressure applied to a cartridge using a pressure sensor.

In accordance with an aspect of the present invention, to accomplish the above and other objects, there is provided a circular stapler including a head cover formed in a tubular shape so that a space is defined therein, a cartridge provided in one end of the head cover to accommodate a staple therein, a staple drive provided inside the head cover to extrude the staple from the cartridge while moving toward the cartridge, a sensor drive provided inside the head cover and configured to come into contact with the cartridge, and a pressure sensor provided inside the head cover to measure a pressure applied to the cartridge by receiving the pressure from the sensor drive.

The sensor drive may include a sensor drive main body formed in an annular shape so that the staple drive passes through a center thereof, the sensor drive main body having one surface that comes into contact with the pressure sensor, and a sensor drive leg portion protruding from the other surface of the sensor drive main body toward the cartridge so that an end thereof comes into contact with the cartridge.

The sensor drive leg portion may include a plurality of sensor drive leg portions protruding along the annular sensor drive main body, and the sensor drive leg portions are arranged to surround the staple drive.

The sensor drive leg portions may be located in respective grooves, which are formed in an outer surface of the staple drive so as to extend in a longitudinal direction of the staple drive.

The pressure sensor may be formed in an annular shape so that the staple drive passes through a center thereof, the pressure sensor having one surface that comes into contact with the sensor drive.

The pressure sensor may be formed in an annular shape so that the staple drive passes through a center thereof, the pressure sensor having one surface that comes into contact with the sensor drive main body, the sensor drive main body may be provided, on one surface thereof, with a first contact protrusion that protrudes in an annular shape, and the pressure sensor may be provided on one surface thereof with a second contact protrusion that protrudes in an annular shape, and the first contact protrusion and the second contact protrusion may come into contact with each other.

The circular stapler may further include a sensor support plate provided inside the head cover so as to come into contact with an surface of the pressure sensor, thereby supporting the pressure sensor.

The cartridge may include a staple accommodating portion for accommodating the staple, an end of the staple drive being inserted into the stable accommodating portion, and a contact portion formed on the staple accommodating portion so as to come into contact with the sensor drive leg portion.

The cartridge may be moved toward the sensor drive when pressure is applied to one surface of the cartridge from which the staple is extruded.

The circular stapler may further include an elastic body for pressing the sensor drive main body so as to be moved away from the pressure sensor by coming into contact with the surface of the sensor drive main body.

The head cover may have one end that is placed in the same plane as one surface of the cartridge from which the staple is extruded, or that protrudes from the surface of the cartridge from which the staple is extruded.

The circular stapler may further include an output unit for providing a user with a visual output, a tactile output, or an audible output when the pressure measured by the pressure sensor reaches a predetermined pressure.

The predetermined pressure may range from 40 kPa to 44 kPa.

The circular stapler may further include an anvil placed to face the cartridge so as to be moved toward the cartridge, the anvil causing the staple to be bent when the staple is extruded from the cartridge, the pressure may be applied to the cartridge when the anvil is moved toward the cartridge after a human tissue is placed between the cartridge and the anvil.

Features and advantages of the present invention will become clearer from the following detailed description with reference to the accompanying drawings.

The terms or words used in the specification and claims of the present invention should not be interpreted using typical or dictionary limited meanings, and should be constructed as meanings and concepts conforming to the technical sprit of the present invention based on the principle that the inventors can appropriately define the concepts of the terms to explain the present invention in the best manner.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
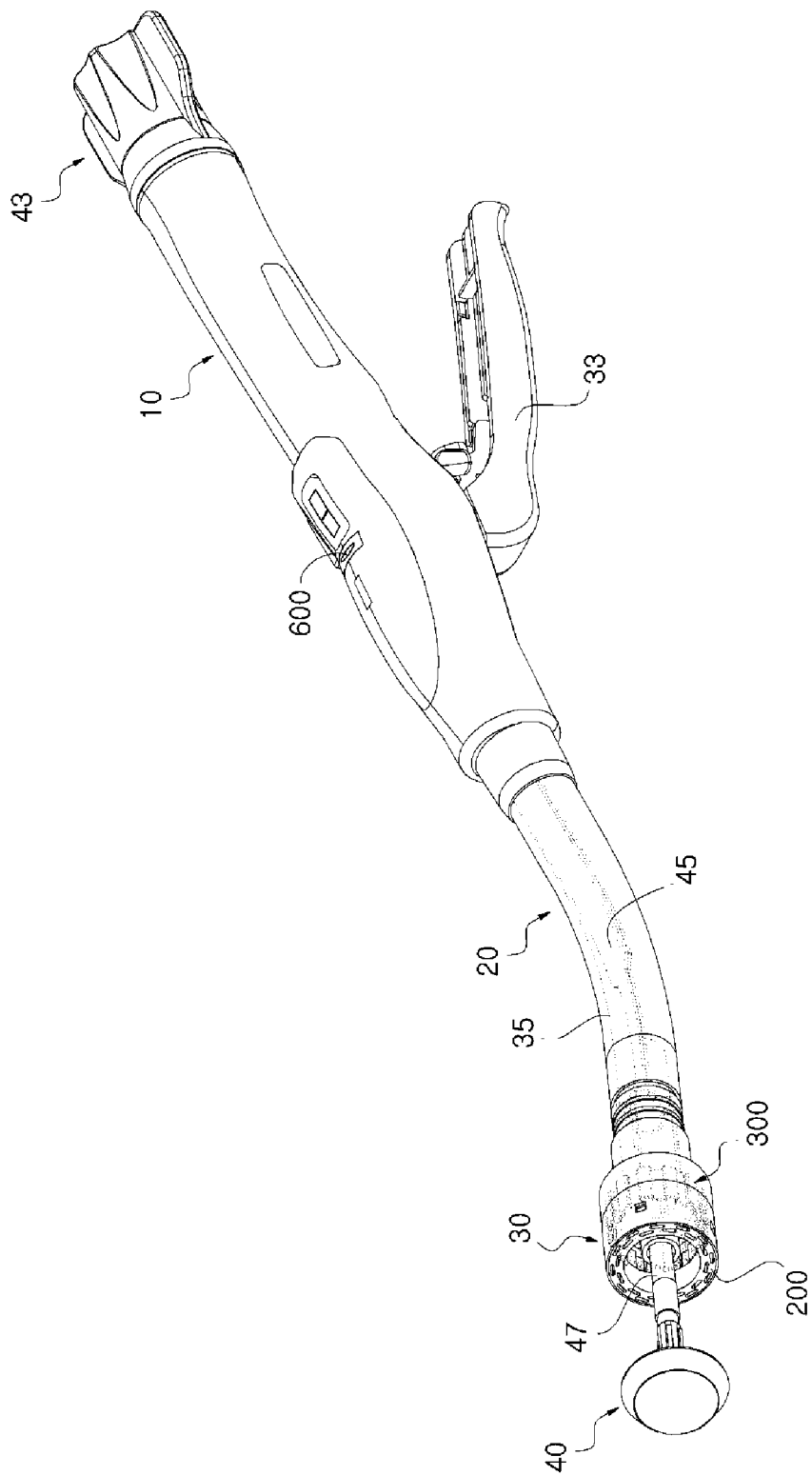
FIG. 1 is a perspective view of a circular stapler according to an embodiment of the present invention.

The objects, specific advantages and novel features of the present invention will become clearer from the following detailed description in conjunction with the accompanying drawings and the exemplary embodiments. In the specification, with regard to reference numerals added to constituent elements illustrated in the respective drawings, it is to be noted that the same constituent elements are designated by the same reference numerals even when they are depicted in different drawings. In addition, the terms "first", "second", "one end", "the other end", etc. are used simply to distinguish any one element from other elements, and the elements are not limited by the terms. In the following description of the present invention, a detailed description of known functions incorporated herein will be omitted when it may make the subject matter of the disclosure rather unclear.

Hereinafter, an exemplary embodiment of the present invention will be described in detail with reference to the accompanying drawings.

Figure 2:
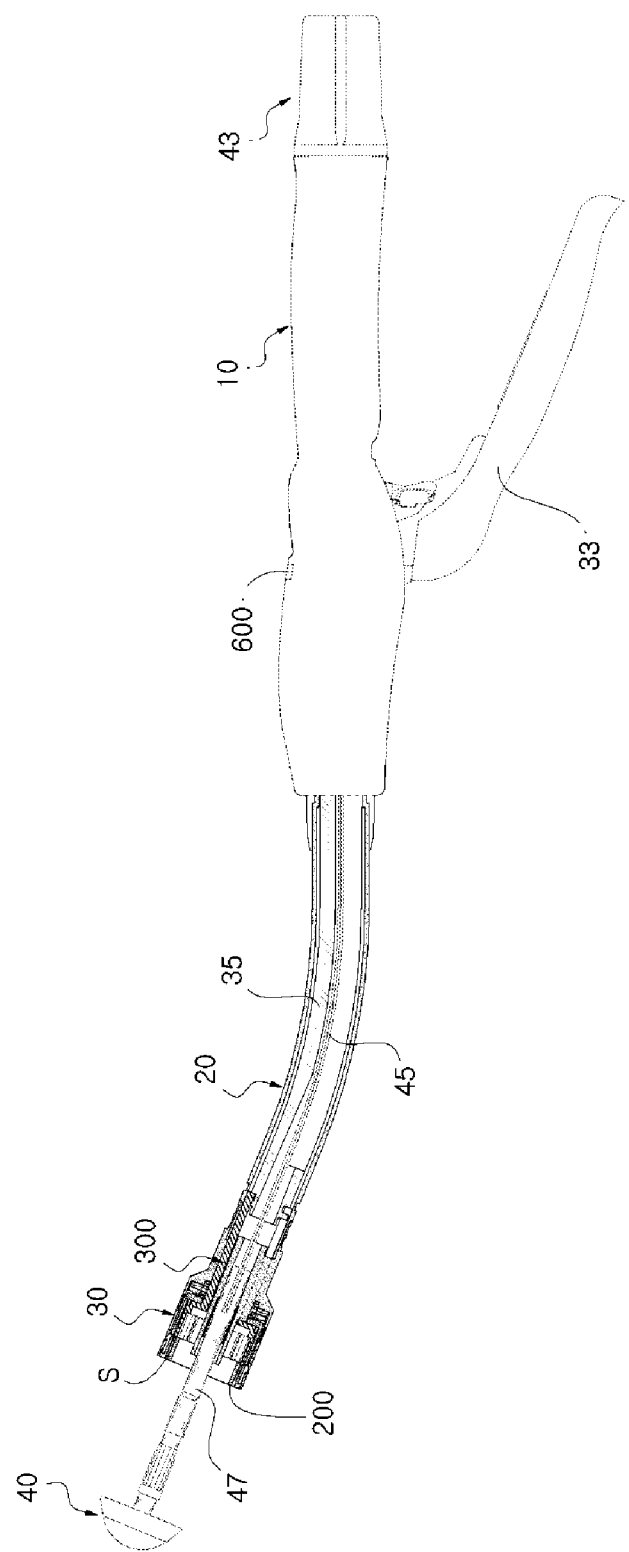
FIG. 2 is a partial sectional view of the circular stapler according to the embodiment of the present invention.

FIG. 1 is a perspective view of a circular stapler according to an embodiment of the present invention, and FIG. 2 is a partial sectional view of the circular stapler according to the embodiment of the present invention.

As illustrated in FIGS. 1 and 2, the circular stapler according to the present embodiment may basically include, for example, a main body 10, a neck 20, a head unit 30, and an anvil 40. Here, an adjusting knob 43 may be provided on the end of the main body 10. The adjusting knob 43 serves to move the anvil 40 by driving a trocar 47, which is exposed from the head unit 30, via a trocar slide 45 provided in the neck 20. That is, when a user rotates the adjusting knob 43, the anvil 40 is moved toward or away from the head unit 30 (more particularly, a cartridge 200). In addition, a trigger 33 is rotatably coupled to one side of the main body 10. The trigger 33 serves to extrude staples S from the cartridge 200 by driving a staple drive 300, which is provided in the head unit 30, via a drive slide 35 provided inside the neck 20. That is, when the user pulls the trigger 33, the staples 3 are extruded from the cartridge 200.

For reference, the above-described configuration is given by way of example, and the circular stapler according to the present embodiment should not be limited to the above-described configuration. With respect to basic constituent elements thereof, configurations of all kinds of circular staplers known in the related art may be employed.

Note that the circular stapler according to the present embodiment includes the head unit 30, which includes, for example, a head cover 100, the cartridge 200, the staple drive 300, a sensor drive 400, and a pressure sensor 500, unlike a circular stapler known in the related art. This configuration will be described below in detail.

Figure 3:
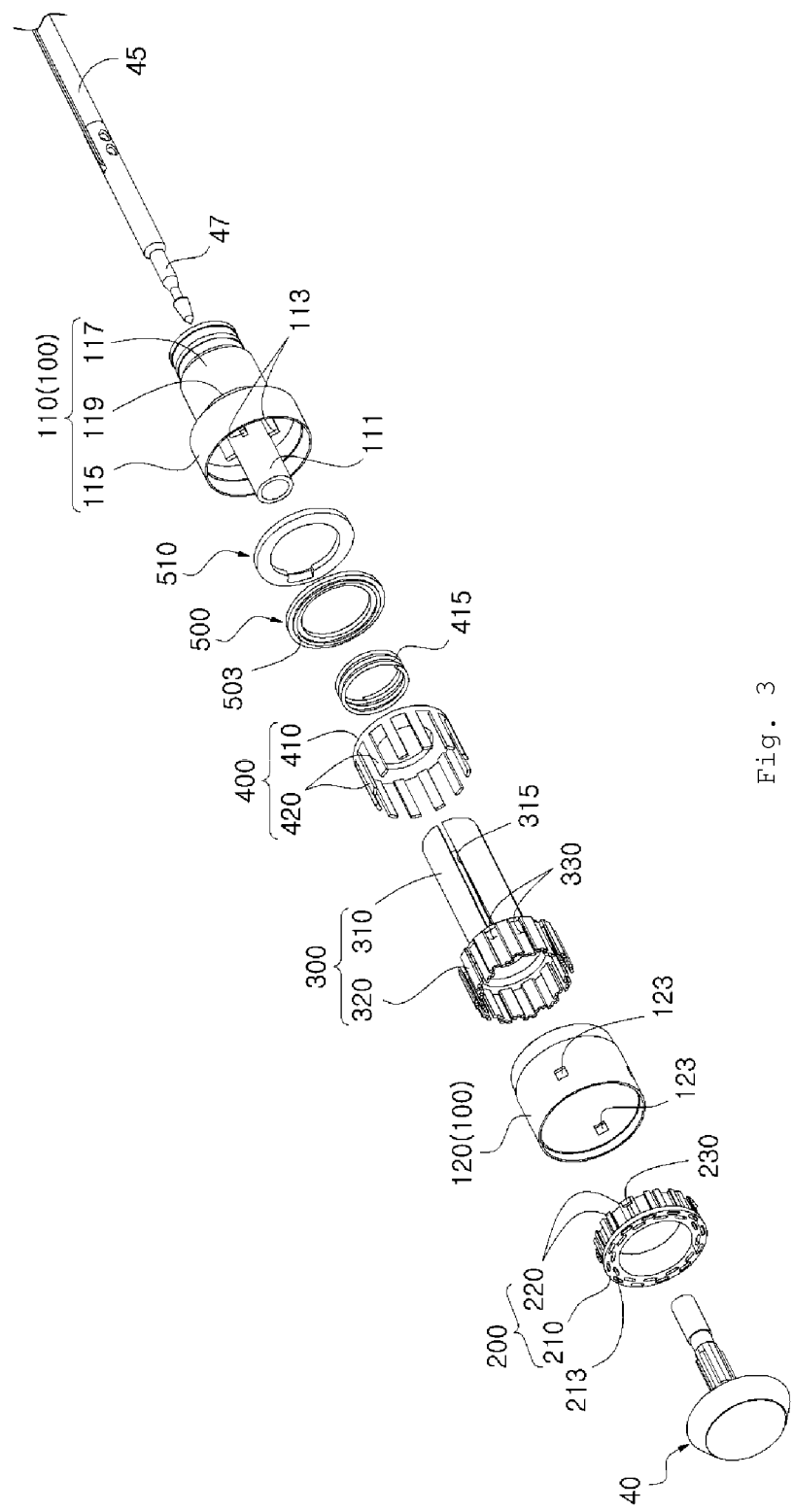
FIG. 3 is a partial exploded perspective view of the circular stapler according to the embodiment of the present invention.
Figure 4:
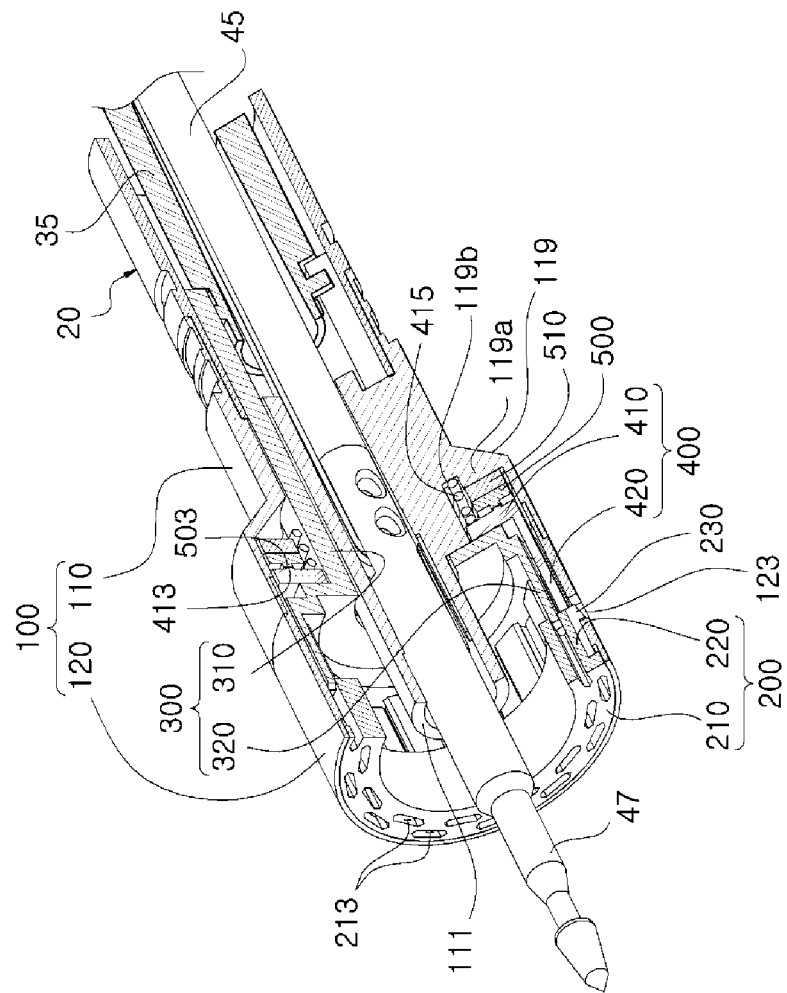
FIG. 4 is a partial cut-away view of the circular stapler according to the embodiment of the present invention.
Figure 4:
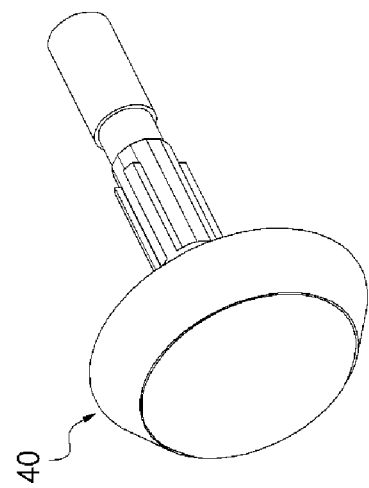

FIG. 3 is a partial exploded perspective view of the circular stapler according to the embodiment of the present invention, and FIG. 4 is a partial cut-away view of the circular stapler according to the embodiment of the present invention.

As illustrated in FIGS. 3 and 4, the circular stapler according to the present embodiment includes the head cover 100, which is formed in a tubular shape so that a space is defined therein, the cartridge 200, which is provided in one end of the head cover 100 and accommodates staples therein, the staple drive 300, which is provided inside the head cover 100 and extrudes staples from the cartridge 200 by moving toward the cartridge 200, the sensor drive 400, which is provided inside the head cover 100 and comes into contact with the cartridge 200, and the pressure sensor 500, which is provided inside the head cover 100 and measures the pressure applied to the cartridge 200 when receiving the pressure from the sensor drive 400.

The head cover 100 is a cover for the head unit 30 and is formed in a tubular shape such that a space is defined therein. The cartridge 200, the staple drive 300, the sensor drive 400, the pressure sensor 500 and the like may be arranged in that sequence from one end of the head cover 100 within the space in the head cover 100. In addition, as illustrated in FIG. 4, the head cover 100 may include a first head cover 110 coupled to the end of the neck 200, and a second head cover 120 coupled to the end of the first head cover 110. At this time, a tubular member 111, through which the trocar 47 may pass, may be formed at the center of the first head cover 110, and the second head cover 120 may be provided with coupling holes 123, into which coupling bosses 230 formed on the outer surface of the cartridge 200 are coupled. More specifically, as illustrated in FIG. 3, the first head cover 110 may include a first cover member 115, which is coupled to the second head cover 120, a second cover member 117, which is coupled to the neck 20 and has a smaller diameter than that of the first cover member 115, and a third cover member 119, which interconnects the first cover member 115 and the second cover member 117. At this time, the third cover member 119 may be provided with a support protruding portion 119a (see FIG. 4) for supporting the pressure sensor 500 (or a sensor support plate 510), which will be described below.

The cartridge 200 serves to accommodate a plurality of staples therein, and is provided in one end of the head cover 100. Here, the cartridge 200 may generally have an annular shape and may include a staple accommodating portion 210 and a contact portion 220. At this time, the staple accommodating portion 210 is configured to accommodate the staples and the end of the staple drive 300 is inserted into the stable accommodating portion 210. When the end of the staple drive 300 is inserted into the staple accommodating portion 210, the staples may be extruded from the staple accommodating portion 210. Specifically, the staple accommodating portion 210 may accommodate the staples in respective staple pockets 213, which extend in the thickness direction of the cartridge 200. When the end (e.g. an extruder portion 320) of the staple drive 300 is inserted into the staple pockets 213, the staples in the staple pockets 213 may be extruded from the staple accommodating portion 210. In addition, the contact portion 220 is formed on the staple accommodating portion 210 so as to come into contact with a sensor drive leg portion 420. The contact portion 220 may serve to transfer the pressure applied to the cartridge 200 to the sensor drive 400. Here, the contact portion 220 may be formed so as to radially protrude from the staple accommodating portion 210. Meanwhile, when pressure is applied to one surface (i.e. the exposed surface) of the cartridge 200, from which the staples are extruded, the cartridge 200 may be moved toward the sensor drive 400. That is, the cartridge 200 may be coupled to the head cover 100 (more particularly, the second head cover 120) so as to be movable only toward the sensor drive 400 in order to transfer the pressure applied to the cartridge 200 to the sensor drive 400. To this end, the coupling bosses 230, which have a hook shape, may be provided on the outer surface of the contact portion 220. The coupling bosses 230 may be coupled into the coupling holes 123 formed in the second head cover 120. At this time, the coupling bosses 230 and the coupling holes 123 function only to prevent the cartridge 200 from moving away from the sensor drive 400, but allow the cartridge 200 to move closer to the sensor drive 400.

Meanwhile, as illustrated in FIG. 4, one end of the head cover 100 (more particularly, the second head cover 120) may be placed in the same plane as one surface (i.e. the exposed surface) of the cartridge 200, from which the staples are extruded, or may protrude from one surface (i.e. the exposed surface) of the cartridge 200, from which the staples are extruded. Accordingly, one surface (i.e. the exposed surface) of the cartridge 200 does not protrude outward from one end of the head cover 100 (more particularly, the second head cover 120). With this configuration, pressure may not be unnecessarily applied to the cartridge 200, and only contact pressure with the anvil 40 transferred through human tissue 700 may be applied to the cartridge 200.

The staple drive 300 serves to extrude the staples from the cartridge 200, and is provided inside the head cover 100 (more particularly, inside the cartridge 200). Here, the staple drive 300 may generally have a tubular shape, and may include a transfer portion 310 and the extruder portion 320. At this time, the transfer portion 310 is connected to the drive slide 35 (see FIG. 4), which is operated by the trigger 33, and the extruder portion 320 protrudes from the end of the transfer portion 310 so as to correspond to the staple pockets 213, thereby actually extruding the staples from the cartridge 200. Specifically, when the drive slide 35 is moved toward the cartridge 200 by the trigger 33, both the transfer portion 310 and the extruder portion 320 of the staple drive 300 may also be moved toward the cartridge 200, thereby extruding the staples from the cartridge 200. Meanwhile, as illustrated in FIG. 3, the transfer portion 310 of the staple drive 300 may be provided with a longitudinal guide slit 315, and the tubular member 111 of the first head cover 110 may be provided with a guide protrusion 113, which is configured to be inserted into the guide slit 315. Accordingly, the staple drive 300 may be stably moved toward the cartridge 200 while being guided by the guide slit 315 and the guide protrusion 113.

The sensor drive 400 serves to transfer the pressure applied to the cartridge 200 to the pressure sensor 500 by coming into contact with the cartridge 200, and is provided inside the head cover 100 (more particularly, inside the cartridge 200). Here, the sensor drive 400 may include a sensor drive main body 410 and the sensor drive leg portion 420. At this time, the sensor drive main body 410 may be formed in an annular shape so that the staple drive 300 may pass through the center of the sensor drive main body 410 and one surface of the sensor drive main body 410 may come into contact with the pressure sensor 500. In addition, the sensor drive leg portion 420 may protrude from the other surface of the sensor drive main body 410 toward the cartridge 200 so as to come into contact at the end thereof with the cartridge 200. Accordingly, the sensor drive 400 may come into contact at one side thereof (i.e. at the sensor drive main body 410) with the pressure sensor 500 and may come into contact at the other side thereof (i.e. at the sensor drive leg portion 420) with the cartridge 200, thereby transferring the pressure applied to the cartridge 200 to the pressure sensor 500.

Specifically, as illustrated in FIG. 3, a plurality of sensor drive leg portions 420 may protrude along the annular sensor drive main body 410. At this time, the sensor drive leg portions 420 may be arranged so as to surround the extruder portion 320 of the staple drive 300. More specifically, the sensor drive leg portions 420 may be located in a plurality of grooves 330, which are formed in the outer surface of the staple drive 300 (more particularly, the extruder portion 320) so as to extend in the longitudinal direction of the staple drive 300. The grooves 330 may be naturally formed due to the shape of the extruder portion 320 of the staple drive 300, which is formed to correspond to the staple pockets 213. As such, because the sensor drive leg portions 420 are located in the grooves 330 of the staple drive 300, there is no interference between the sensor drive leg portions 420 and the staple drive 300, which enables the staple drive 300 to be moved toward the cartridge 200.

In addition, an elastic body 415 may be additionally provided so as to come into contact with one surface of the sensor drive main body 410. The elastic body 415 may apply pressure to the sensor drive main body 410 so that the sensor drive body 410 is moved away from the pressure sensor 500. Thanks to the elastic body 415, the sensor drive 400 does not transfer unnecessary pressure to the pressure sensor 500 until pressure is applied to the cartridge 200. That is, the pressure sensor 500 may maintain an initial value at zero owing to the elastic body 415. Specifically, the elastic body 415 may be, for example, a spring, and may come into contact at one end thereof with one surface of the sensor drive main body 410 and may be supported at the other end thereof by a support recess 119b (see FIG. 4) formed in the head cover 100 (more particularly, the third cover member 119).

The pressure sensor 500 serves to measure the pressure applied to the cartridge 200 by receiving the pressure from the sensor drive 400 and is provided inside the head cover 100 (more particularly, inside the sensor drive 400). Here, the pressure sensor 500 may generally be formed in an annular shape so that, for example, the staple drive 300 and the elastic body 415 pass through the center of the pressure sensor 500, and one surface of the pressure sensor 500 may come into contact with the sensor drive 400 (more particularly, the sensor drive main body 410). Accordingly, the pressure sensor 500 may measure the pressure applied to the cartridge 200 by receiving the pressure through the sensor drive leg portions 420 and the sensor drive main body 410. In addition, as illustrated in FIG. 4, a first contact protrusion 413 may be formed in an annular shape on one surface of the sensor drive main body 410, and a second contact protrusion 503 may be formed in an annular shape on one surface of the pressure sensor 500. At this time, the first contact protrusion 413 and the second contact protrusion 503 may come into contact with each other. Due to the first contact protrusion 413 and the second contact protrusion 503, the contact area between the sensor drive main body 410 and the pressure sensor 500 may be reduced, which may increase the sensitivity of the pressure sensor 500.

Meanwhile, although the pressure sensor 500 may be, for example, a Force Sensing Resistor (FSR) sensor, a strain gauge, or a piezoelectric element, of course, all kinds of known pressure sensors may be employed without limitation thereto.

In addition, a sensor support plate 510 may be provided to support the other surface of the pressure sensor 500 (i.e. the surface on the opposite side relative to the surface that comes into contact with the sensor drive main body 410). Here, the sensor support plate 510 may be provided inside the head cover 100 so as to come into contact with the other surface of the pressure sensor 500, and may generally be formed in an annular shape so that, for example, the staple drive 300 and the elastic body 415 pass through the center of the sensor support plate 510. At this time, the sensor support plate 510 may be shaped to correspond to the shape of the pressure sensor 500 so as to support a sufficiently wide area of the pressure sensor 500. In addition, the sensor support plate 510 may be supported by the support protruding portion 119a formed on the head cover 100 (more particularly, the third cover member 119). Note that the sensor support plate 510 does not need to be provided separately from the head cover 100, and may be integrally formed with the head cover 100 so as to support the pressure sensor 500.

Meanwhile, when the pressure measured by the pressure sensor 500 reaches a predetermined pressure, an output unit 600 (see FIGS. 1 and 2) may provide the user with visual output, tactile output, or audible output. For example, the output unit 600 may be an LED display, which is mounted on the main body 10 and provides visual output by emitting light when the measured pressure reaches a predetermined pressure. The user may recognize the optimum contact pressure thanks to the output of the output unit 600.

In addition, although the aforementioned predetermined pressure may vary depending on the kind of human tissue 700, it may range from 40 kPa to 44 kPa, which is the minimum contact pressure not causing leakage, and most preferably, may be 42 kPa. When the predetermined pressure is below 40 kPa, leakage may occur. When the predetermined pressure exceeds 44 kPa, stenosis or necrosis may occur.

Figure 5:
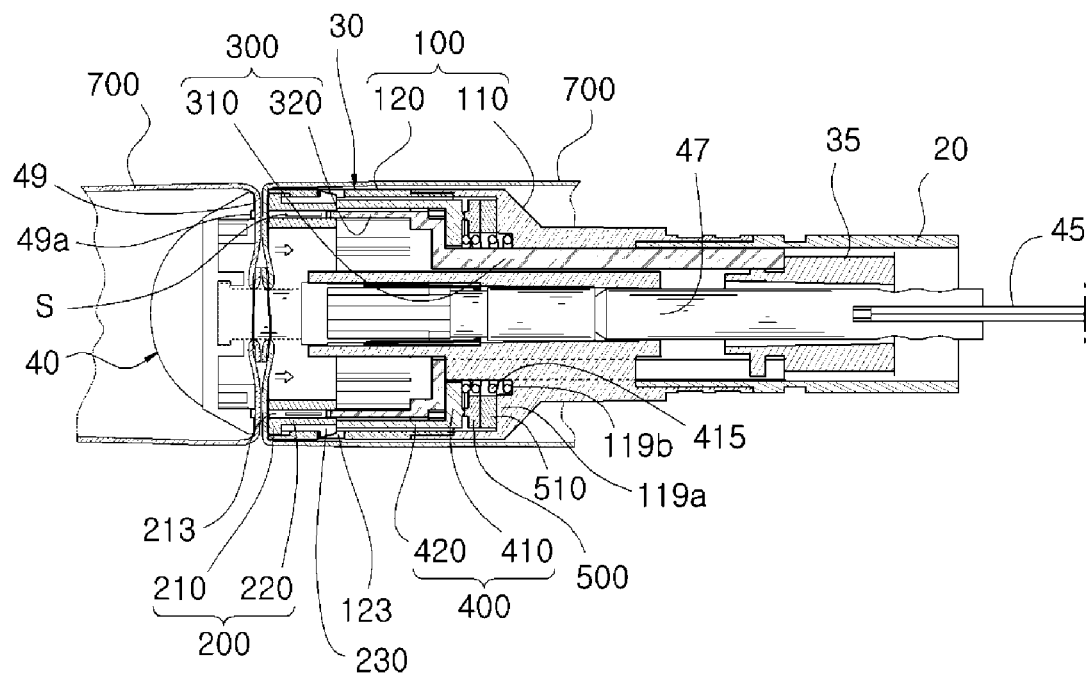
FIG. 5 is a sectional view of the circular stapler according to the embodiment of the present invention.

Meanwhile, the circular stapler according to the present embodiment further includes the anvil 40. Here, as illustrated in FIG. 5, the anvil 40 is coupled to the trocar 47 so as to face the cartridge 200, and is movable toward the cartridge 200 via the movement of the trocar 47. At this time, the anvil 40 includes an opposite end surface 40, which faces one surface (i.e. the exposed surface) of the cartridge 200, from which the staples S are extruded, and a guide pocket 49a is formed in the opposite end surface 49. The guide pocket 49a causes the staple S to be bent in a butterfly shape when the staple S is extruded from the cartridge 200. As described above, when the anvil 40 is moved toward the cartridge 200, pressure may be applied to the cartridge 200. Specifically, when the anvil 40 is moved toward the cartridge 200 after two layers of human tissue 700 are placed between the cartridge 200 and the anvil 400, the two layers of human tissue 700 are compressed between the cartridge 200 and the anvil 40, whereby pressure is applied to the cartridge 200. As such, the pressure applied to the cartridge 200 may be measured by the pressure sensor 500 by way of the sensor drive 400.

Figure 6:
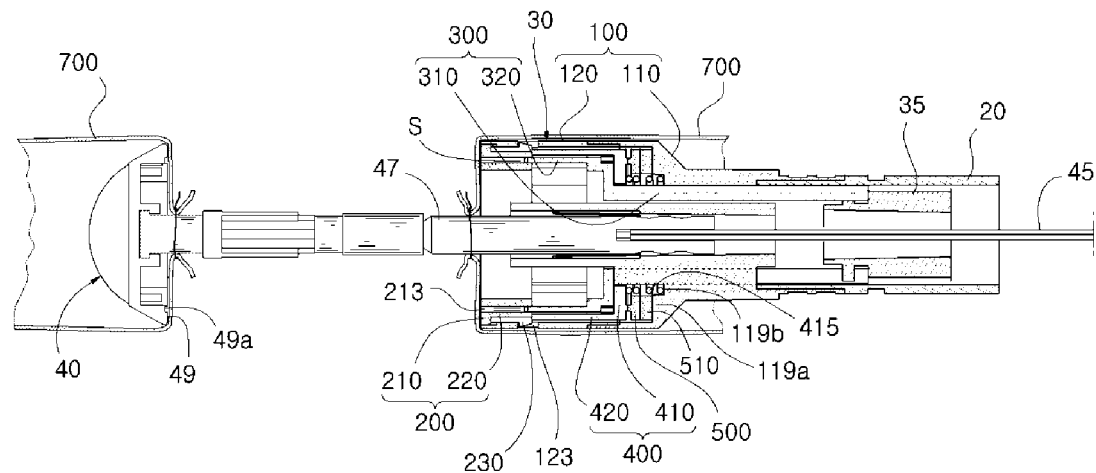
FIGS. 6 to 8 are sectional views illustrating the process of operating the circular stapler according to the embodiment of the present invention.
Figure 7:
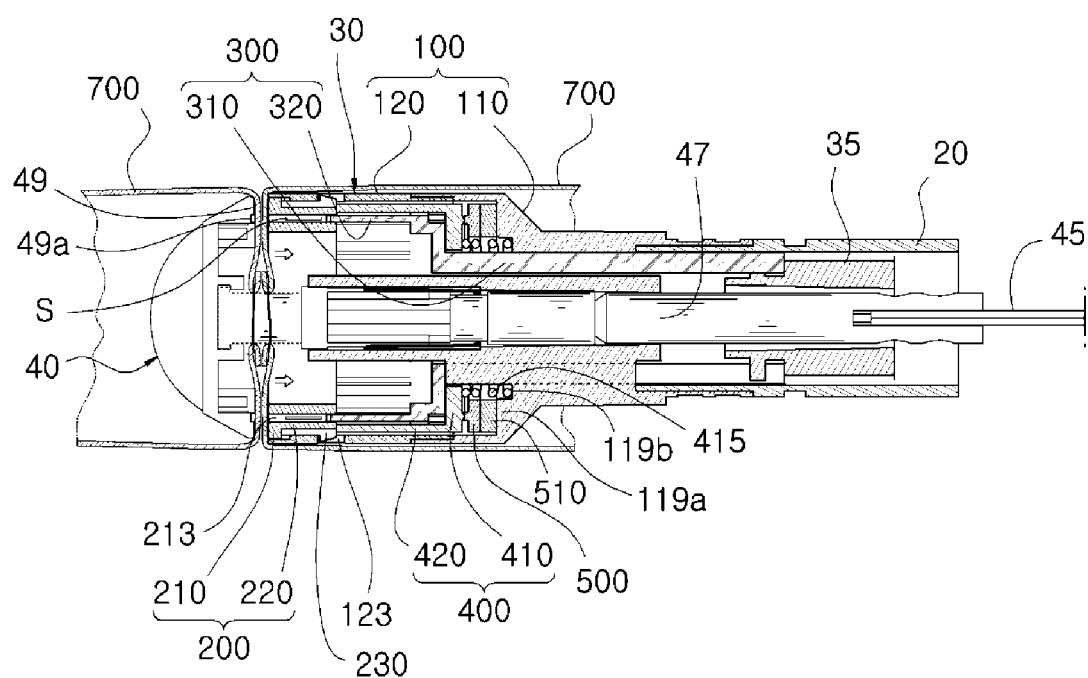
Figure 8:
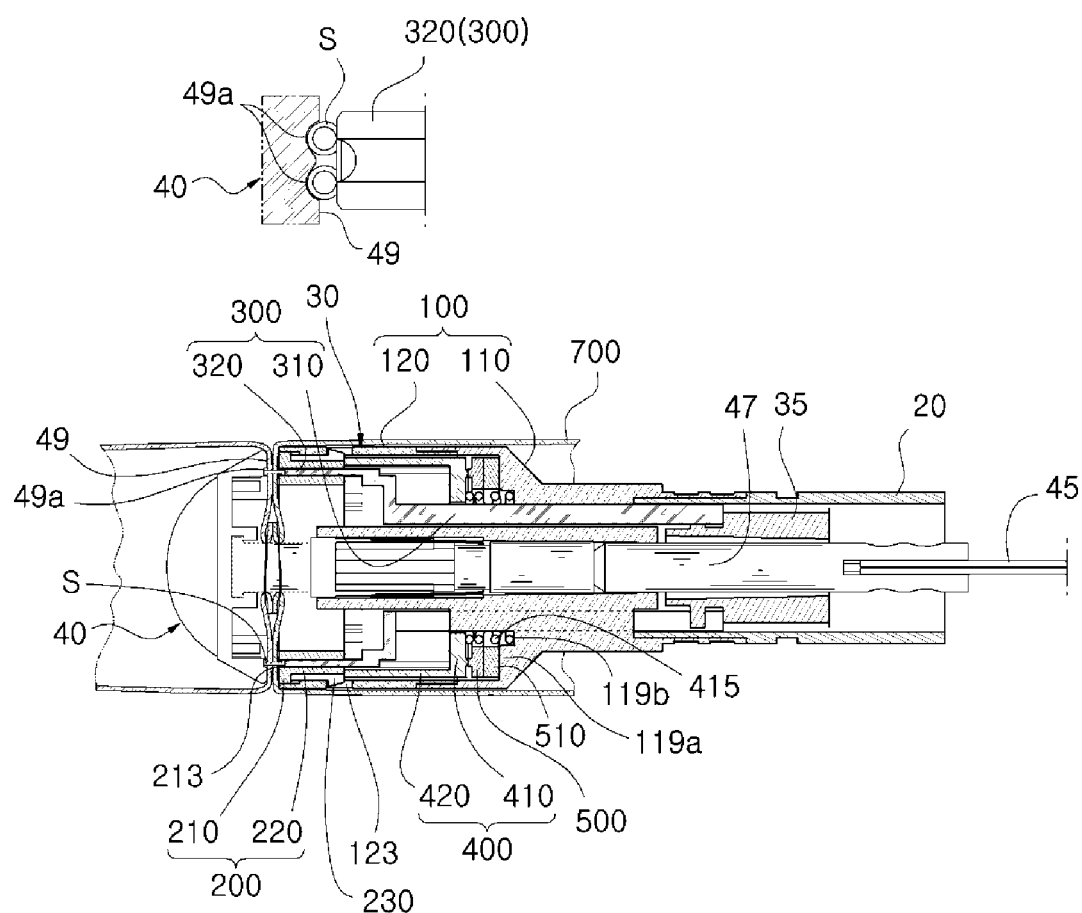

FIGS. 6 to 8 are sectional views illustrating the process of operating the circular stapler according to the embodiment of the present invention, and the process of operating the circular stapler according to the present embodiment will be described below with reference to FIGS. 6 to 8.

First, as illustrated in FIG. 6, two layers of human tissue 700 are respectively arranged and fixed near the anvil 40 and the head unit 300 (more particularly, the cartridge 200). At this time, the anvil 40 may be completely spaced apart from the cartridge 200. In addition, because the sensor drive 400 is pressed by the elastic body 415 so as to be moved away from the pressure sensor 500, no unnecessary pressure is transferred to the pressure sensor 500.

Next, as illustrated in FIG. 7, the anvil 40 is moved toward the head unit 30 (more particularly, the cartridge 200) as the user rotates the adjusting knob. When the anvil 40 is moved close to the cartridge 200, the two layers of human tissue 700 are compressed between the anvil 40 and the cartridge 200, causing pressure to be applied to the cartridge 200 (see the arrows). As such, the pressure applied to the cartridge 200 is transferred to the pressure sensor 500 through the sensor drive leg portions 420 and the sensor drive main body 410. At this time, the pressure sensor 500 measures the pressure transferred from the sensor drive 400 in real time. When the measured pressure reaches a predetermined pressure (i.e. the minimum contact pressure not causing leakage, for example, within a range from 40 kPa to 44 kPa) as the anvil 40 becomes close to the cartridge 200, the output unit 600 (see FIGS. 1 and 2) provides output (e.g. visual output, tactile output or audible output). Through the output of the output unit 600, the user may be made aware that an appropriate amount of pressure is being applied to the two layers of human tissue 700. Accordingly, the user may stop the movement of the anvil 40 toward the cartridge 200 when the output unit 600 provides the output.

Next, as illustrated in FIG. 8, when the staple drive 300 is driven as the user pulls the trigger 33, the staples S are extruded from the cartridge 200. The staples S extruded from the cartridge 200 penetrate the two layers of human tissue 700, and thereafter are bent in a butterfly form by the guide pocket 49a formed in the opposite end surface 49 of the anvil 40 to thereby perform coupling.

As is apparent from the above description, the circular stapler according to the present embodiment may measure the pressure applied to the cartridge 200 (i.e. the pressure applied to the two layers of human tissue 700 placed between the anvil 40 and the cartridge 200) using the pressure sensor 500. Thereby, the circular stapler may couple the two layers of human tissue 700 using the staples S after appropriately setting the contact pressure thereof, which may completely prevent, for example, leakage, stenosis or necrosis.

In addition, according to the present invention, when the pressure measured by the pressure sensor 500 reaches a predetermined pressure, the output unit 600 may provide the user with, for example, visual output, tactile output or audible output, which may allow the user to recognize the optimum contact pressure when treating enteroanastomosis.

Although the embodiments of the present invention have been described above in detail, it is clear that the above description is merely given to concretely describe the present invention and the present invention is not limited thereto, and that alterations or improvements thereof are possible by those skilled in the art within the scope of the present invention.

The simplified alterations and modifications of the present invention fall within the scope of the present invention, and the concrete protection range of the present invention will be made clear by the accompanying claims.

| Reference numerals | |
|---|---|
| 10: main body | 20: neck |
| 30: head unit | 33: trigger |
| 35: drive slide | 40: anvil |
| 43: adjusting knob | 45: trocar slide |
| 47: trocar | 49: opposite end surface |
| 49a: guide pocket | 100: head cover |
| 110: first head cover | 111: tubular member |
| 113: guide protrusion | 115: first cover member |
| 117: second cover member | 119: third cover member |
| 119a: support protruding portion | 119b: support recess |
| 120: second head cover | 123: coupling holes |
| 200: cartridge | 210: staple accommodating portion |
| 213: staple pocket | 220: contact portion |
| 230: coupling bosses | 300: staple drive |
| 310: transfer portion | 315: guide slit |
| 320: extruder portion | 330: grooves |
| 400: sensor drive | 410: sensor drive main body |
| 413: first contact protrusion | 415: elastic body |
| 420: sensor drive leg portion | 500: pressure sensor |
| 503: second contact protrusion | 510: sensor support plate |
| 600: output unit | 700: human tissue |
| S: Staple | |

What is claimed is:

1. A circular stapler comprising:
   a head cover formed in a tubular shape so that a space is defined therein;
   a cartridge provided in one end of the head cover to accommodate a staple therein;
   a staple drive provided inside the head cover to extrude the staple from the cartridge while moving toward the cartridge;
   a sensor drive provided inside the head cover and configured to come into contact with the cartridge; and
   a pressure sensor provided inside the head cover to measure a pressure applied to the cartridge by receiving the pressure from the sensor drive;
   wherein the sensor drive comes into contact at one side thereof with the pressure sensor and comes into contact at another side thereof with the cartridge, thereby transferring the pressure applied to the cartridge to the pressure sensor;
   further comprising an anvil placed to face the cartridge so as to be moved toward the cartridge, the anvil causing the staple to be bent when the staple is extruded from the cartridge,
   wherein the pressure is applied to the cartridge when the anvil is moved toward the cartridge after a human tissue is placed between the cartridge and the anvil.

2. The stapler according to claim 1, wherein the sensor drive includes:
   a sensor drive main body formed in an annular shape so that the staple drive passes through a center thereof, the sensor drive main body having one surface that comes into contact with the pressure sensor; and
   a sensor drive leg portion protruding from the other surface of the sensor drive main body toward the cartridge so that an end thereof comes into contact with the cartridge.

3. The stapler according to claim 2, wherein the sensor drive leg portion includes a plurality of sensor drive leg portions protruding along the annular sensor drive main body, and the sensor drive leg portions are arranged to surround the staple drive.

4. The stapler according to claim 3, wherein the sensor drive leg portions are located in respective grooves, which are formed in an outer surface of the staple drive so as to extend in a longitudinal direction of the staple drive.

5. The stapler according to claim 2, wherein the cartridge includes:
   a staple accommodating portion for accommodating the staple, an end of the staple drive being inserted into the staple accommodating portion; and
   a contact portion formed on the staple accommodating portion so as to come into contact with the sensor drive leg portion.

6. The stapler according to claim 2, further comprising an elastic body for pressing the sensor drive main body so as to be moved away from the pressure sensor by coming into contact with the surface of the sensor drive main body.

7. The stapler according to claim 2, wherein the pressure sensor is formed in an annular shape so that the staple drive passes through a center thereof, the pressure sensor having one surface that comes into contact with the sensor drive main body,
   wherein the sensor drive main body is provided, on one surface thereof, with a first contact protrusion that protrudes in an annular shape, and the pressure sensor is provided on one surface thereof with a second contact protrusion that protrudes in an annular shape, and
   wherein the first contact protrusion and the second contact protrusion come into contact with each other.

8. The stapler according to claim 1, wherein the pressure sensor is formed in an annular shape so that the staple drive passes through a center thereof, the pressure sensor having one surface that comes into contact with the sensor drive.

9. The stapler according to claim 1, further comprising a sensor support plate provided inside the head cover so as to come into contact with a surface of the pressure sensor, thereby supporting the pressure sensor.

10. The stapler according to claim 1, wherein the cartridge is moved toward the sensor drive when pressure is applied to one surface of the cartridge from which the staple is extruded.

11. The stapler according to claim 1, wherein the head cover has one end that is placed in the same plane as one surface of the cartridge from which the staple is extruded, or that protrudes from the surface of the cartridge from which the staple is extruded.

12. The stapler according to claim 1, further comprising an output unit for providing a user with a visual output, a tactile output, or an audible output when the pressure measured by the pressure sensor reaches a predetermined pressure.

13. The stapler according to claim 12, wherein the predetermined pressure ranges from 40 kPa to 44 kPa.

* * * * *